United States Patent [19]
Coughlin et al.

[11] Patent Number: 5,925,529
[45] Date of Patent: Jul. 20, 1999

[54] METHOD FOR DISCOVERY OF PEPTIDE AGONISTS

[75] Inventors: Shaun R. Coughlin, Tiburon; Ji Chen; Harold Bernstein, both of San Francisco, all of Calif.; Maki Ishii, Kyoto, Japan; Ling Wang; Mian Chen, both of San Francisco, Calif.

[73] Assignee: The Regents of the University of California, Oakland, Calif.

[21] Appl. No.: 08/483,506

[22] Filed: Jun. 7, 1995

[51] Int. Cl.$^6$ .......................... G01N 33/53; G01N 33/543
[52] U.S. Cl. ................. 435/7.2; 435/7.1; 435/4; 436/519; 436/518
[58] Field of Search ................. 435/7.2, 4, 7.1; 530/403; 436/519, 518

[56] References Cited

U.S. PATENT DOCUMENTS 5,223,409   6/1993   Ladner et al. ..................... 435/69.7

OTHER PUBLICATIONS

Matthews et al, Biochemistry, vol. 33, pp. 3266–3279, (1994).
Barnard et al., G Protein–Coupled Receptors for ATP and Other Nucleotides: A New Receptor Family, TiPS, 15:67–70 (1994).
Chen et al., Thrombin Receptor Activation, Journal of Biological Chemistry, 269(23):16041–16045 (1994).
Cwirla et al., Peptides on Phage: A Vast Library of Peptides for Identifying Ligands, Proc. Natl. Acad. Sci., 87:6378–6382 (1990).
Inglese et al., Structure and Mechanism of the G Protein–Coupled Receptor Kinases; Journal of Biological Chemistry, 268(32):2735–2738 (1993).
Lam et al., A New Type of Synthetic Peptide Library for Identifying Ligand–Binding Activity, Nature, 354:82–86 (1991).
Larhammar et al., The Receptor Revolution–Multiplicity of G–Protein–Coupled Receptors, Drug Design and Discovery, 9:179–188 (1993).
Lefkowitz, G Protein–Coupled Receptor Kinases, Cell, 74:409–412 (1993).
Thien–Khai et al., Molecular Cloning of a Functional Thrombin Receptor Reveals a Novel Proteolytic Mechanism of Receptor Activation; Cell, 64:1057–1068 (1991).
Scarborough et al., Tethered Ligand Agonist Peptides, The Journal of Biological Chemistry. 267:19:13146–13149, Jul. 05, 1992.
Scott et al., Searching for Peptide Ligands with an Epitope Library, Science 249:386–390, Jul. 27, 1990.

*Primary Examiner*—Ponnathapura Achutamurthy
*Assistant Examiner*—T. D. Wessendorf
*Attorney, Agent, or Firm*—Cooley Godward LLP

[57] ABSTRACT

This invention relates to peptide ligand discovery and is particularly directed to a method for the discovery of agonists for membrane bound receptors. The inventive detection system involves the use of a "tethered" ligand for probing receptor binding. The general detection system includes a membrane, a membrane bound receptor, and a chimeric ligand presenting molecule. This chimeric protein forms the tethered ligand and in turn includes a membrane domain, a linker domain, a ligand domain, and a cleavable terminal domain. The "ligands" of the system are exposed by the addition of a specific peptidase that cleaves at the designated sequence. The sequence of the ligand that produces signal as a result of the interaction between the agonist and receptor can be then be isolated using sib selection.

15 Claims, 5 Drawing Sheets

METHOD FOR DISCOVERY OF PEPTIDE AGONISTS

ACKNOWLEDGEMENTS

This invention was made with government support under Grant No. HL44907, awarded by the National Institutes of Health. The U.S. Government has certain rights in this invention.

INTRODUCTION

Technical Field

This invention is in the field of peptide ligand discovery and is particularly directed to a method for the discovery of agonists for membrane-bound receptors.

SUMMARY OF THE INVENTION

An object of this invention is to provide a method for facilitating the discovery of peptide ligands for receptors.

Another object of this invention is to provide a screening method for agonists for membrane bound receptors, particularly G protein coupled receptors.

Another object of this invention is to provide a general method for constructing random peptide libraries for specifically activating membrane bound receptors.

Another object of this invention is to provide for a detection system that facilitates the practice of the disclosed invention.

These and other objects of the invention as will hereinafter become more readily apparent through further discussion in this specification have been accomplished by providing a method for the identification of an agonist for a receptor, which comprises (1) preparing a detection system comprising a biological membrane; a receptor inserted in the biological membrane; and a chimeric peptide-presenting molecule inserted in the membrane, wherein the peptide-presenting molecule has membrane and external domains comprising, in the order stated (a) a cleavable terminal domain; (b) a peptide library domain; (c) a linker domain; and (d) a membrane domain; wherein the cleavable terminal domain is cleavable from the peptide library domain by a specific peptidase; (2) adding the specific peptidase to the detection system, whereby the cleavable terminal domain is cleaved from the peptide library domain; and (3) detecting a signal produced by the receptor as a result of interaction of the peptide library domain with the receptor. A detection system comprising the various molecular component used in the method and an appropriate biological membrane are also provided along with an expression system for preparing the peptides.

BRIEF DESCRIPTION OF THE DRAWINGS

The invention will be better understood when considered by reference to the following examples of specific embodiments and to the figures that form part of this specification, wherein.

DESCRIPTION OF SPECIFIC EMBODIMENTS

Previous methods of using random peptide libraries have included displaying peptides on various surfaces such as resin beads, silica chips, and other supports including biological vectors such as bacteriophage. While these methods are generally useful for screening for antagonists, these systems are not readily adapted to screen for agonists. The present invention presents a peptide display library in the context of membranes that is especially well suited to screening for agonists for membrane bound receptors.

Figure 1A:
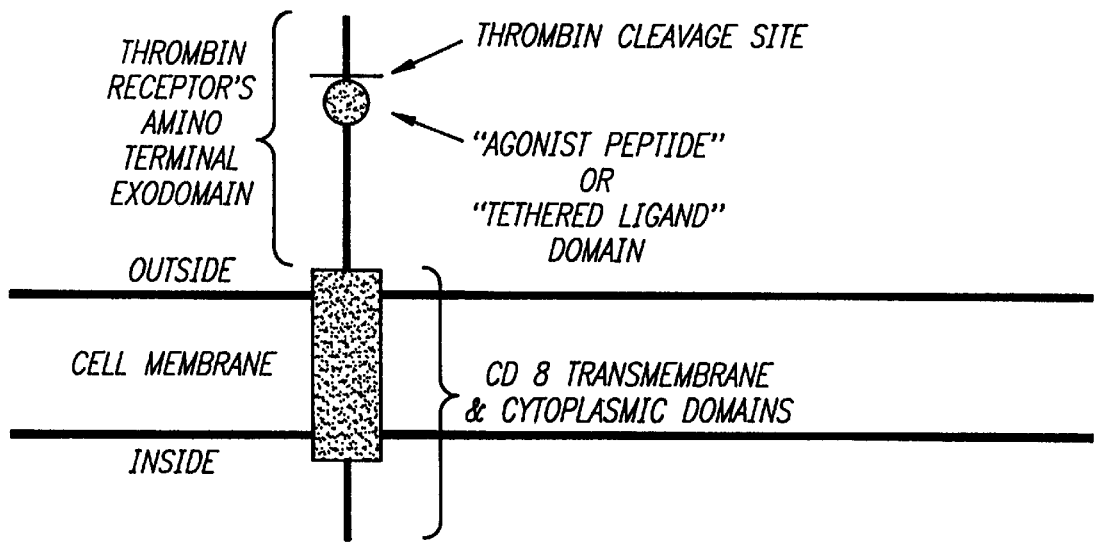
FIG. 1A is a schematic diagram showing various features of the library. A random pentapeptide is encoded so as to be unmasked by thrombin cleavage and remain tethered to the cell membrane.
Figure 1B:
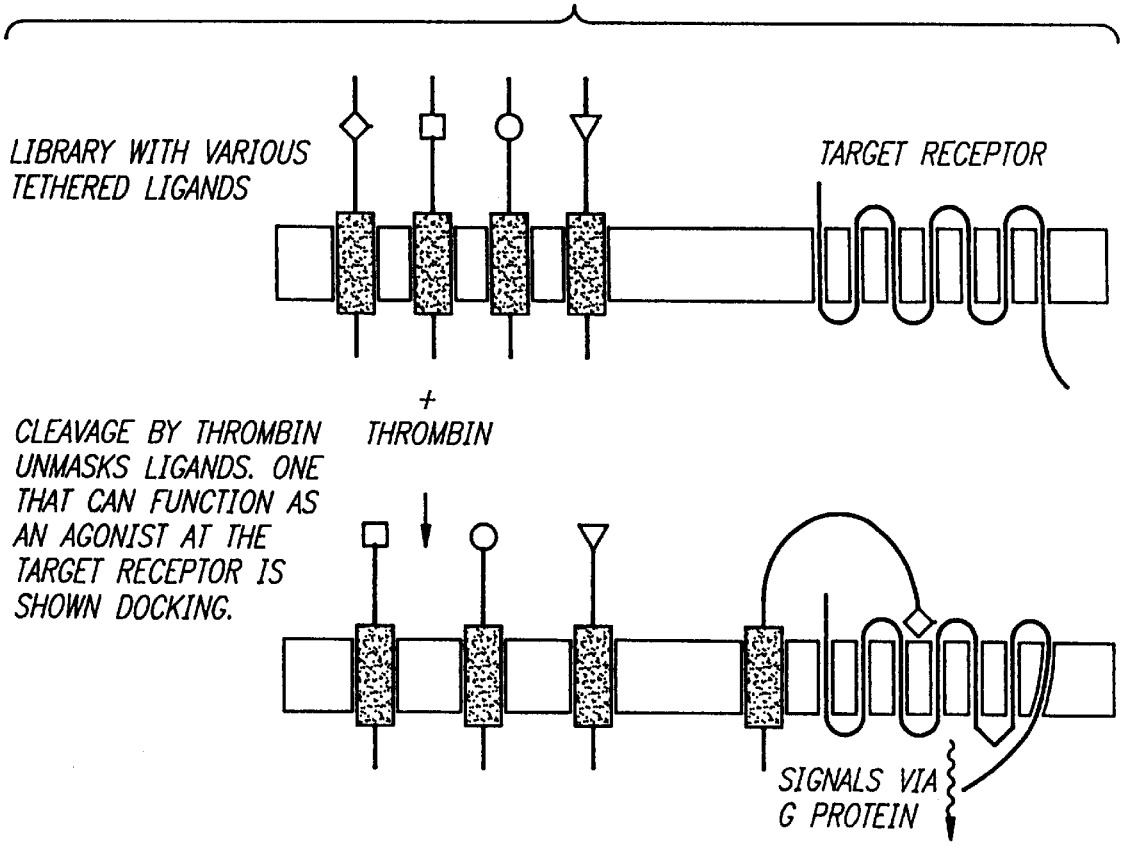
FIG. 1B is a schematic diagram showing how the library works. The library is co-expressed with a target receptor which, when activated, gives a convenient detectable signal in cells. In the example shown in this specification the library and target receptor were co-expressed in Xenopus oocytes and the readout was $^{45}$Ca efflux. Thrombin was added to unmask the random peptides. One or a few are able to recognize and activate the target receptor, causing cell signaling. In the example reported below, we screened 6000 clones from the library in each oocyte.

An essential feature of the present invention is the use of a "tethered ligand" for probing receptor binding. A ligand is literally tethered to the membrane by the use of a ligand presenting molecule (chimeric peptide-presenting molecule) comprising a cleavable terminal domain, a ligand domain (peptide library domain), a linker domain, and a membrane domain. A schematic for one embodiment of the invention is shown in FIG. 1A. A unique feature of this system is that the exposure of the ligand domain is specifically controlled through the insertion of a peptidase cleavage site between the terminal domain and the ligand domain.

By varying the peptide sequence of the ligand domain, various peptide libraries can be constructed using established techniques well known in the relevant art. Smith, G. P., Science 228:1315–1317 (1985); Cwirla, S. E. et al, PNAS 87: 6378–6382 (1990). The resulting library is then screened against a specific membrane bound receptor. By monitoring the relevant signal associated with the specific membrane receptor, sequences that act as ligands, particularly as agonists, can be readily discovered.

One effect of "tethering" is the increase in the effective concentration of the ligand by localizing it to the cell surface. By restricting the ligand to the plane of the membrane (2-dimensional space versus 3-dimensional space), tethering confers a tremendous kinetic advantage to this detection system and allows for sufficient sampling.

Each of the components to the general method of the invention will be discussed in turn for a better understanding of the invention as a whole. To reiterate, the detection system comprises a membrane, a membrane bound receptor, and a chimeric ligand presenting molecule (also referred to as a peptide-presenting molecule). This chimeric protein forms the tethered ligand and in turn comprises a membrane domain, a linker domain, a ligand domain (also referred to as a peptide library domain), and a cleavable terminal domain. The "ligands" of the system are exposed by the addition of a specific peptidase that cleaves at the designated sequence. The sequence of the ligand that produces signal as a result of the interaction between the agonist and receptor can be isolated using sib selection. Vu et al., Cell 64: 1057–1068 (1991).

The term "agonist" means a molecule that activates a receptor to generate a "signal" the receptor normally generates. The generated signal is receptor dependent.

The term "receptor" means a large biological macromolecule that transmits a signal from one side of the membrane to the other side of the membrane upon binding of an agonist. A large and versatile superfamily of receptors is the G protein coupled receptors. Some examples of biological functions mediated by the G protein coupled receptors include hormone action, neurotransmission, chemotaxis, perception of light, smell, and taste, and regulation of blood pressure, heart rate, and blood clotting.

Although the present invention will often be carried out with a naturally occurring receptor, modified or even chimeric receptors can be used. For example, receptor modifications can include the substitution, insertion, and/or deletions of one or more amino acid residues. The substitution of amino acids will usually be as a result of the needs of the construction, providing for convenient restriction sites, ease of manipulation, improvement in levels of expression, or the like. The insertion and/or deletions of receptor amino acids will be for similar reasons.

Another component of the detection system is the biological membrane into which both the receptor and the ligand presenting molecule are inserted. The biological membrane is usually part of a living cell and uses the normal cellular machinery to carry out the biological operations described herein, such as the production of the signal induced by binding to the receptor. However, it is possible to use biological membranes that are not part of living cells as long as sufficient materials are provided to allow the receptor to produce its signal. For example, artificial membranes can be used, such as liposomes containing cytoplasm. But because of the associated increased cost and difficulty of operation, production of such artificial membrane constructs are not generally preferred.

The ligand presenting molecule is a chimeric protein comprising a transmembrane domain, a linker domain, a ligand domain, and a cleavable terminal domain. The transmembrane domain is the anchor that confines the ligand domain to the membrane and will generally have from about 25 amino acids. Many examples of transmembrane domains exist. For instance, any seven transmembrane domain from a single transmembrane domain receptor, such as PDGF, EGF, FGF, VEGF, growth hormone, and TNF, can be used.

The next segment of the peptide-presenting molecule is the linker domain. Although this domain is usually a part of the single peptide sequence that makes up the overall molecule, its only function is to be a flexible linker ("rope") between the membrane domain and the peptide library domain. This flexibility allows the "ligand" on the ligand presenting molecule to interact with the target receptor. The length can vary and can be receptor dependent. In one preferred embodiment, the linker is between 20 and 50 amino acids in length.

The ligand domain is where the peptide sequence is randomized to construct the peptide library. Although this can be any length in theory, the upper limit to a workable library is probably approximately $10^9$ variants. If the peptide is relatively short, such as a pentapeptide or a hexapeptide, all possible peptides can be generated. However, if certain position within a peptide sequence are fixed, then longer peptides can be used without exceeding the limits of a workable library.

The essential feature of a cleavable terminal domain is a sequence that is specifically recognized and cleaved by a peptidase. Especially preferred are highly specific proteases such as thrombin and enteropeptidase. Other proteases that can be used in this capacity include coagulation proteases such as Factors VIIa, Xa, XIa, and IXa, and converting enzymes such as angiotensin converting enzyme, and interleukin 1 converting enzymes.

The cleavable terminal domain is an engineered cleavage site between the N-terminal end and the adjacent peptide library domain that may or may not be associated with a signal sequence. If a signal sequence is used, it can be selected independently from the remainder of the sequence of the peptide presenting molecule. For example, ATE-CD8 includes a signal sequence at its amino terminus to direct the chimeric protein to the plasma membrane in the appropriate orientation. The signal sequence is cleaved off by a signal peptidase to generate the mature protein. In some cases, the terminal domain will be selected to provide specificity for the protease that will be used to cleave off the terminal domain so that the peptide domain can bind to a receptor. In other cases, other portions of the peptide presenting molecule will provide the desired specificity, usually acting at least in part in concert with the cleavable terminal domain.

A component of the detection system that is not inserted in the membrane is a specific peptidase that is used to cleave the terminal domain from the peptide library domain. In preferred cases, the specific peptidase does not require the peptide library domain for cleavage site recognition, but relies on the sequence of other portions of the peptide-presenting molecule, typically the cleavable terminal domain.

In preferred embodiments, the peptidase is thrombin and the peptide linker, peptide library domain, and terminal domain together comprise a thrombin receptor amino-terminal exodomain, with the proviso that a sequence SFLLR (SEQ ID NO:4) of the exodomain is replaced by a different sequence in the different members of the peptide library. A particularly preferred embodiment of the chimeric ligand-presenting protein, particularly for G protein coupled receptors, is ATE-CD8. ATE-CD8 encodes a protein consisting of the epitope-tagged thrombin receptor's amino terminal exodomain up to and including receptor residue aspartic acid$^{91}$ (Asp$^{91}$) fused to CD8 at the extracellular aspect of CD8's single transmembrane domain at C8 residue isoleucine$^{162}$ (Ile$^{162}$). Littman et al., Cell 40:237–246 (1985); J. Chen et al., Biol. Chem. 269:16041–16045 (1994).

In an alternative embodiment, the chimeric peptide-presenting molecule further comprises a cytoplasmic domain that interacts with the cytoplasmic domain of a receptor to produce a signal upon binding of the chimeric peptide-presenting molecule to the receptor. In these cases, the cytoplasmic domain of both peptide-presenting molecule and receptor comprise monomeric members of a dimeric signal-generating complex. Examples of such receptor systems include those receptors having tyrosine kinase activity. The inclusion of a functional cytoplasmic domain such as the tyrosine kinase reporter expands the repertoire of receptors that can be used in the practice of the present invention.

Figure 3A:
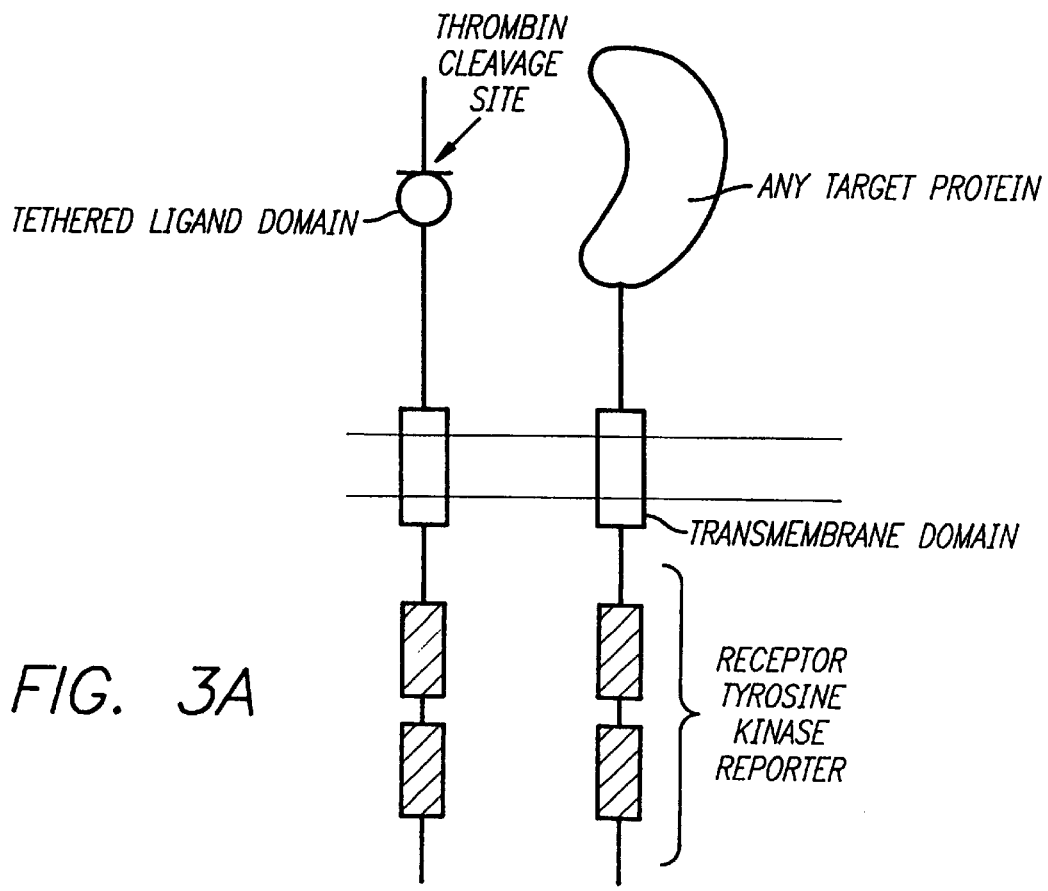
FIG. 3A is a schematic diagram showing one embodiment of the invention in which a library of ligand-presenting proteins includes a receptor tyrosine kinase domain displayed on its cytoplasmic face. These domains signal when brought into proximity with another receptor tyrosine kinase domain. By building a target (any protein for which a ligand is sought) that is tethered to a transmembrane domain and receptor tyrosine kinase domain, a system will detect the formation of heterodimers of library members and target receptors.
Figure 3B:
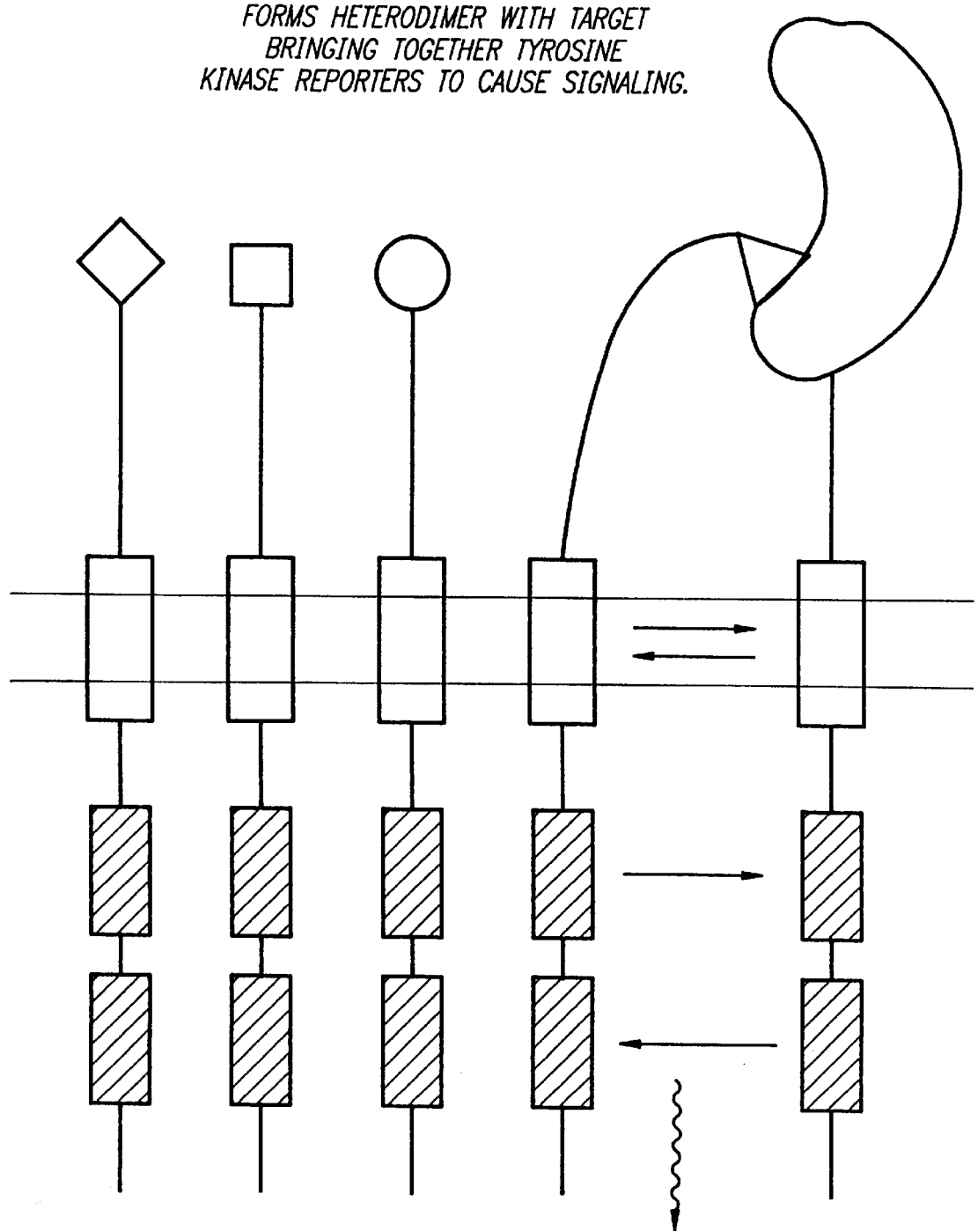
FIG. 3B is a schematic diagram that shows operation of the embodiment shown in FIG. 3A.

An illustration of this concept is shown in FIG. 3 where a tyrosine kinase domain is additionally coupled to ATE-CD8. The tyrosine kinase reporter in this case is derived from the platelet-derived growth factor receptor tyrosine kinase (PDGFRTK) domain. The dimerization of the cytoplasmic PDGFRTK region leads to intermolecular phosphorylation of this domain allowing coupling to downstream signaling molecules. In Xenopus oocytes, this results in $^{45}$Ca mobilization.

The chimeric constructs can be prepared using conventional methods that are well known in the relevant art. Since chimeric constructs are generally comprised of natural sequences, standard techniques for isolating and manipulating natural genes can be similarly used. One can prepare the truncated portion of the sequence by employing the polymerase chain reaction (PCR) using appropriate primers. Alternatively, one can use primer repair, where the sequence of interest can be cloned in an appropriate host. In either case, the resulting termini allows for the proper annealing of the sequences for encoding the chimeric protein.

The practice of the present invention is not limited to any particular method of DNA synthesis or construction for the component parts. Generally, the reactions for oligonucleotide synthesis are performed on a solid phase support by first coupling the 3' end of the first monomer to the support. The second monomer is added to the 5' end of the first monomer in a condensation reaction to yield a dinucleotide coupled to the solid support. At the end of each coupling reaction, the by-products and unreacted, free monomers are washed away so that the starting material for the next round of synthesis is the pure oligonucleotide attached to the support. In this reaction scheme, the stepwise addition of individual monomers to a single, growing end of a oligonucleotide ensures accurate synthesis of the desired sequence. Moreover, unwanted side reactions are eliminated, such as the condensation of two oligonucleotides, resulting in high product yields. The synthesized DNA then can be purified by any art-recognized technique, e.g., by high-pressure liquid chromatography (HPLC) or PAGE.

Random peptide libraries are formed by random nucleotide sequences for the region coding the ligand domain. One method of randomizing the nucleotide sequences is the addition of equal proportions of all four nucleotides in the monomer coupling reactions. The resulting random incorporation of all nucleotides yields a population of oligonucleotides coding random amino acid sequences. However, this approach has a built-in bias due to the redundancy of the genetic code. Because there are sixty-four possible triplet codons and only twenty amino acids, those that are coded multiple times tend to be over-represented. However, this resulting bias is generally not a problem for agonist screening.

Nevertheless, the amino acid bias can be alleviated by synthesizing the DNA from nucleotide triplets. Here, a triplet coding for each of the twenty amino acids is synthesized from individual monomers. Once synthesized, the triplets are used in the coupling reactions instead of individual monomers. By mixing equal proportions of the triplets, synthesis of oligonucleotides with random codons can be accomplished.

In another embodiment, one can use the random codon generation technique described in U.S. Pat. No. 5,264,563. This technique entails the sequential coupling of monomers to produce oligonucleotides' with random codons. The coupling reactions for the randomization of twenty codons which specify the amino acids of the genetic code are performed in ten different reaction vessels. Each reaction vessel contains a support on which the monomers for two different codons are coupled in three sequential reactions. One of the reactions couple an equal mixture of two monomers such that the final product has a sequence of two different codons. The codons are randomized by removing the supports from the reaction vessels and mixing them to produce a single batch of supports containing all twenty codons. Synthesis at the next codon position proceeds by equally dividing the mixed batch of supports into ten reaction vessels as before and sequentially coupling the monomers for each pair of codons. The supports are again mixed to randomize the codons at the position just synthesized. The cycle of coupling, mixing and dividing continues until the desired number of codon positions have been randomized. After the last position has been randomized, the oligonucleotides with random codons are cleaved from the support.

The technique described in U.S. Pat. No. 5,264,563 is particularly useful as it provides for control of randomization; i.e., sequences can be prepared that are totally random, fixed in some codon positions but random elsewhere, selectively biased toward particular codons, or any combination of the above.

The described detection system has been successfully used to discover novel peptide agonists for two receptors, the formyl peptide receptor and the thrombin receptor.

Formyl peptide receptor

Figure 2:
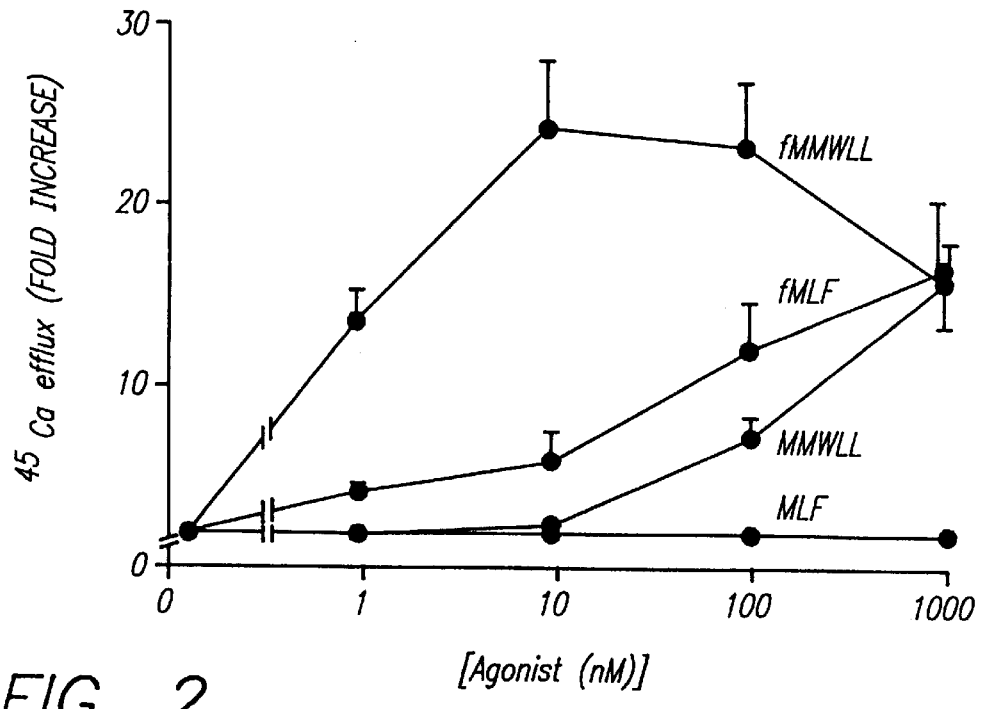
FIG. 2 is a graph showing that a synthetic peptide discovered using the method of the invention (MMWLL) (SEQ ID NO:1) functions as an agonist at the fMLF receptor and that the formylated version of this peptide (fMMWLL) (SEQ ID NO:2) is more potent than fMLF (SEQ ID NO:12) itself.

The formyl peptide receptor was co-expressed with pools representing 10,000 independent clones from the tethered ligand library. A pool of agonist activity was immediately identified. Eleven subpools of 800 independent clones each were screened for activity at the formyl peptide receptor. The most active of these was serially subdivided. Eventually, a single cDNA that conferred thrombin-dependent signaling was identified as MMWLL (SEQ ID NO:1) by sib selection. When a synthetic peptide having the sequence MMWLL was synthesized and tested, it was found to be almost as active as the classical formyl peptide receptor agonist, f-MLF (formyl-Met-Leu-Phe) (SEQ ID NO:12) (FIG. 2). This novel peptide agonist, MMWLL (SEQ ID NO:1), displayed similar structure activity relationships to those published in the literature for known formyl peptide receptor agonists. Freer et al., Biochemistry 19: 2404–2410 (1980); Freer et al., Biochemistry 21: 257–263 (1982).

However, given the lack of an N-terminal formyl group, the level of activity shown by the MMWLL (SEQ ID NO:1) peptide was surprising. It has been previously suggested that the formyl group of f-MLF (SEQ ID NO:12) is essential for significant biological activity. Freer et al., Biochemistry 19: 2404–2410 (1980); Schiffman et al., PNAS 72: 1059–1062 (1975). For example, the unformylated MLF (SEQ ID NO:13) has at least 1000 fold less activity. As expected, the addition of an N-formyl group to MMWLL (SEQ ID NO:2) resulted in increase potency and yielded an agonist more potent than f-MLF (SEQ ID NO:12) itself (FIG. 2).

Thrombin receptor

Figure 4:
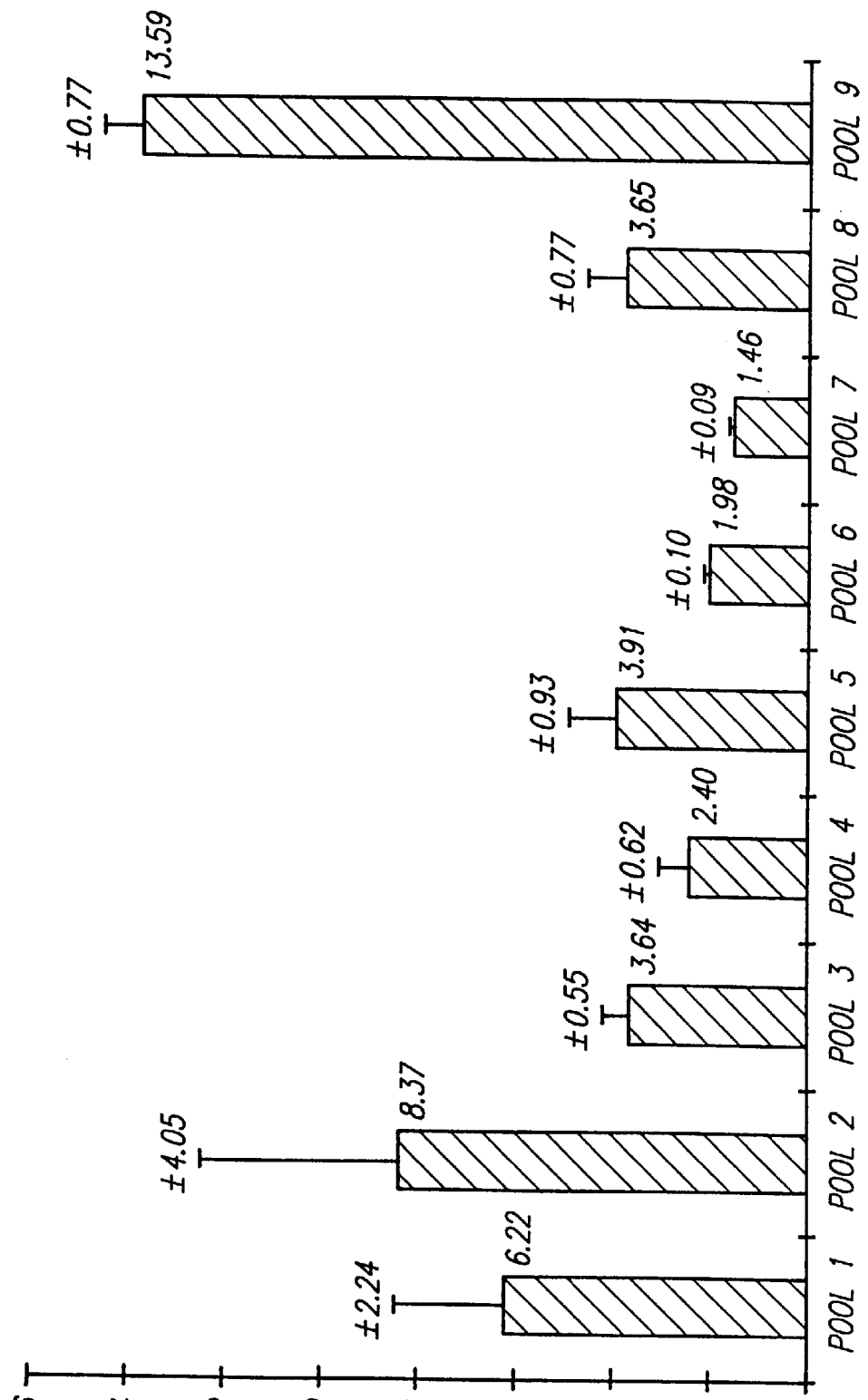
FIG. 4 is a bar graph showing thrombin-induced $^{45}$Ca release from oocytes co-expressing a first set of library pools with the F43A mutant thrombin receptor described in the example below.

Pools of the tethered ligand library (with each pool representing 4000 independent clones) were co-expressed with a mutant thrombin receptor (F43A) that lacks its own functional tethered ligand. A mutant receptor was necessary in this case; otherwise the wild-type receptor would act as its own ligand. The mutant, F43A, could be activated by free synthetic agonist peptide but could not be activated by thrombin. As a result, the signaling in response to thrombin in the co-expression system reflected the intermolecular interaction of the receptor with a member of the library and not with its own amino terminal exodomain. Of the first 9 pools tested, 3 clearly conferred thrombin dependent signaling (FIG. 4). From the most active of these pools, a single clone that conferred signaling was isolated by sib selection.

Figure 5A:
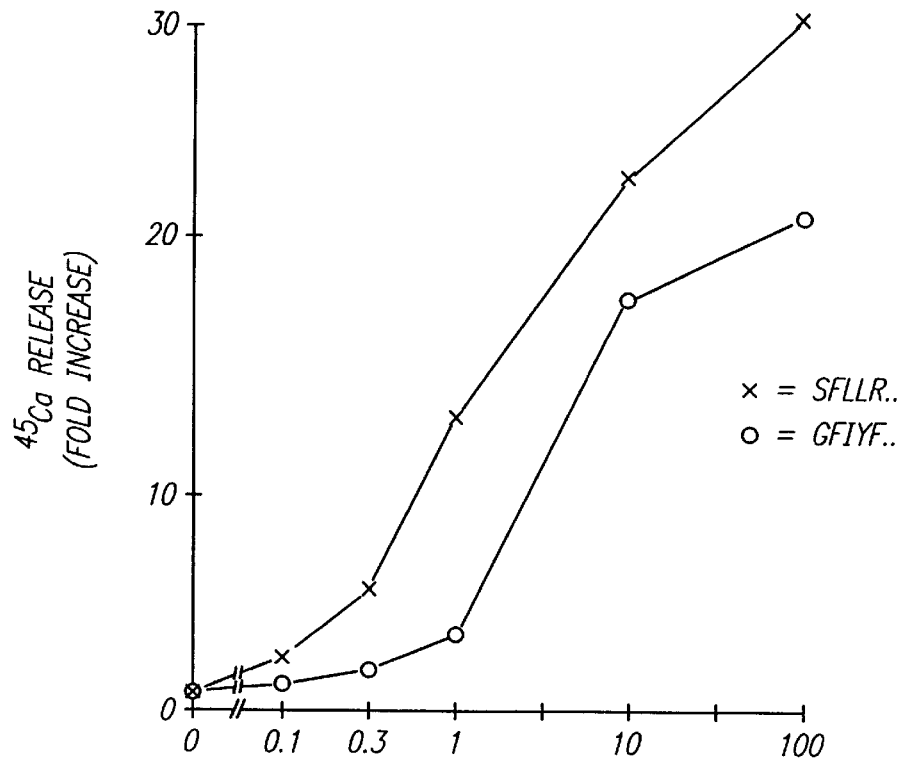
FIG. 5A is a graph showing thrombin receptor response to a new small peptide agonist containing the sequence GFIYF (SEQ ID NO:3) (o—o) as well as response to a similar peptide with the natural agonist sequence-SFLLR (SEQ ID NO:4) (x—x).
Figure 5B:
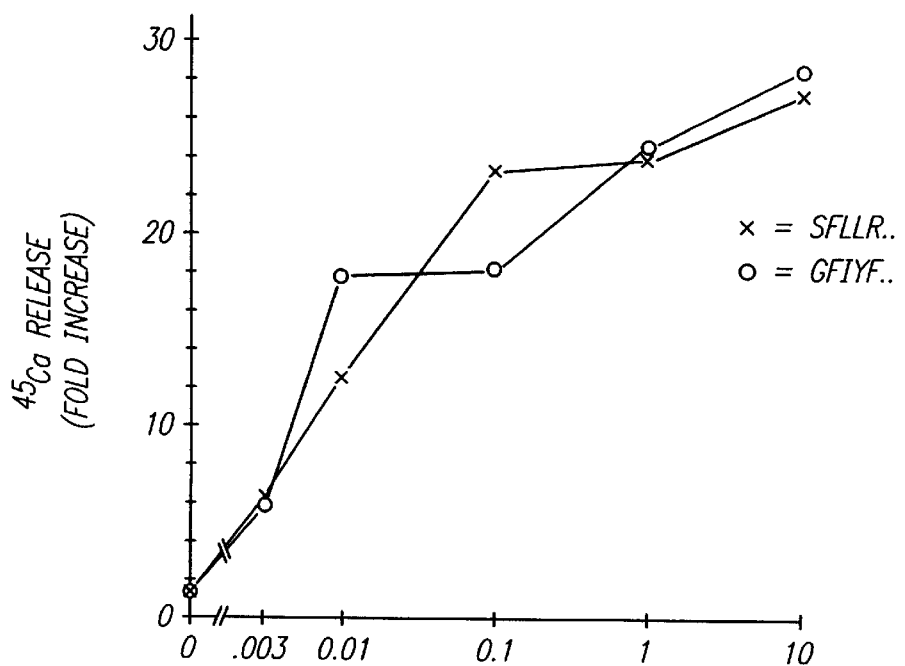
FIG. 5B is a graph showing dose response of both wild-type thrombin receptor (x—x) and a mutant thrombin receptor containing the new sequence GFIYF (SEQ ID NO:3) (o—o) to thrombin activation, which shows that similar responses are obtained.

The sequence of the tethered ligand domain was found to be GFIYF (SEQ ID NO:3). When the peptide was synthesized and tested, it was nearly as effective as the SFLLR (SEQ ID NO:4) peptide which mimics the native tethered ligand sequence (FIG. 5A). Moreover, a mutant thrombin receptor in which the GFIYF (SEQ ID NO:3) sequence replaced the native SFLLR (SEQ ID NO:4) sequence signaled as effectively as the wild type receptor in response to thrombin (FIG. 5B).

The sequence of this new agonist is striking in the context of known thrombin receptor agonist peptide sequences (Table 1). The protonated amino group at the N-terminal of all thrombin receptor peptide agonists, the group corresponding to that created by thrombin cleavage, is critical for agonist function. Other known structure activity relationship include: small neutral residues are preferred at agonist position 1; the conserved phenylalanine at position 2 is critical for agonist function; and, hydrophobic residues are preferred at positions 3 and 4. Surprisingly, all these features are effectively captured in the sequence GFIYF (SEQ ID NO:3). The tethered ligand library sequence method thus "evolved" an agonist which shares critical features with the known naturally occurring thrombin receptor tethered ligand sequences. However, a unique feature of the GFIYF (SEQ ID NO:3) agonist, is its lack of a basic residue. All of the known sequences have an arginine at either position 3 or 5. One possible interpretation of this result is that the arginine plays a role outside of receptor activation.

TABLE 1

| New agonist | GFIYF (SEQ ID No:3) |
| Human | SFLLR (SEQ ID No:4) |
| Rodent | SFFLR (SEQ ID No:5) |
| Xenopus | TFRIF (SEQ ID No:6) |

Comparison of thrombin receptor agonist peptides. The amino acid sequence of the new thrombin receptor agonist derived from the tethered ligand library is compared to the naturally occurring tethered ligand/agonist peptide domains of the human[1], hamster[2], rat[3], and mouse[24], and Xenopus[21].

EXAMPLES

Example 1:

A construct dubbed ATE-CD8 encoding the thrombin receptor's amino terminal exodomain (ATE) fused to the transmembrane domain of CD8 was used to display the receptor's amino terminal exodomain on the cell surface. Chen et al., J. Bio. Chem. 269: 16041–16045 (1994). Surface expression of the encoded protein and its cleavage by thrombin was verified as the presence and thrombin-dependent loss of an epitope placed amino to the thrombin cleavage site. Chen et al., J. Bio. Chem. 269: 16041–16045 (1994); Ishii et al., J. Biol. Chem. 268: 9780–9786 (1993). A library of such molecules in which the receptor's agonist peptide domain SFLLR (SEQ ID NO:4) (closed sphere) was replaced by random pentapeptides was constructed as follows. ATE-CD8 was modified to introduce paired BstXI sites flanking the agonist peptide domain so that a "BstXl cassette" could later be inserted to make the library. An in-frame nonsense mutation was inserted between these sites to ensure early termination of translation of any non-recombinant ATE-CD8 molecules occurring in the library. The modified ATE-CD8 was inserted into pBLOG so as to be flanked by Xenopus globin mRNA 5' and 3' untranslated sequence and sense with respect to an SP6 RNA polymerase promoter. pBLOG was made by subcloning an 0.9 kb EcoRI/PstI fragment from pFROG into the corresponding sites of pBluescript II SK⁻ (Stratagene) in which the BstXI site had been destroyed. BstX1 inserts for the library were generated by annealing a pool of degenerate oligonucleotides 5'-GTACCCCGG(NNK)₅AACCCCAATGATAAATATGAACCATT-3' (SEQ ID NO:7), where N=A, C, G or T in equimolar amounts and K=G or T in equimolar amounts with two complementary, flanking 13-mers 5'-GAATCTAGGGGCC-3' (SEQ ID NO:8) and 5'-GTTCATATITATC-3' (SEQ ID NO:9). Cwirla et al., PNAS 84: 8573–8577 (1987). The annealed oligomers were then ligated into the new BstXI sites of the ATE-CD8 mutant in pBLOG. *E. coli* strain DH10B was electroporated with an aliquot of the resulting library and plated at a complexity of 4000/pool. Of 10 randomly picked clones sequenced, 8 indeed encoded the wild-type ATE-CD8 sequence except for the 15 nucleotides encoding the random agonist pentapeptide; 2 had mutations probably arising during annealing or ligation. Thus, approximately 80% of the library encoded molecules which would display random pentapeptides at their amino termini upon cleavage by thrombin.

Example 2:

Oocytes

Xenopus oocytes were harvested from female Xenopus laevis and processed using published techniques. Coleman, A., In Transcription and Translation: A Practical Approach, Oxford: IRL Press, pp. 271–302 (1984); Williams et al., PNAS 85: 4939–4943 (1988). To remove follicular cells, oocytes were incubated for 4 hr at room temperature with 1 mg/ml Sigma type II collagenase in modified Barth's solution (MBSH) without $Ca^{2+}$, then washed and incubated overnight at 18° C. in MBSH II (MBSH containing 1 mg/ml bovine serum albumin, 1 ml/ml Ficoll, 100 U/ml penicillin, 100 µg/ml streptomycin, and 50 µg/ml gentamicin). Dumont stage V oocytes were selected and microinjected with 5 to 50 nl of mRNA (1 µg/µl in 10 mM HEPES, pH 7.0). Microinjected oocytes were cultured for 24 hr at 18° C. in MBSH then selected for functional assays.

Assays

Agonist-induced increases in $^{45}Ca^{2+}$ release were assessed by published techniques. Williams et al., PNAS 85:4939–4943 (1988). Briefly, intracellular $Ca^{2+}$ pools were labeled by incubating groups of 30 oocytes in 300 µl of $Ca^{2+}$-free MBSH containing 50 µCi of $^{45}CaCl_2$ (10–40 mCi per mg of $Ca^{2+}$) for 4 hr at room temperature. The labeled oocytes were washed and then incubated in MBSH II without antibiotics for 90 min. Groups of five oocytes were selected and placed in individual wells in a 24-well tissue culture plate containing 0.5 ml per well of MBSH II without antibiotics. This medium was removed and replaced with fresh medium every 10 min. The harvested medium was analyzed by scintillation counting to determine $^{45}Ca^{2+}$ release by the oocytes during each 10 min incubation. The 10 min incubations were continued until a stable baseline of $^{45}Ca^{2+}$ release per unit time was achieved. At this point, two additional 10 min collections were obtained, then medium including agonist was added and agonist-induced $^{45}Ca^{2+}$ release determined.

Example 3:

Thrombin-induced $^{45}Ca$ release from oocytes co-expressing the first set of library pools and the F43A mutant thrombin receptor. cRNA was transcribed from cDNA representing pools of 4000 independent clones. Vu et al., Cell 64: 1057–1068 (1991). Xenopus oocytes were co-injected with 25 ng each of library cRNA and F43A mutant thrombin receptor and cultured for 24 h, after which thrombin-stimulated $^{45}Ca$ release was assessed. Results (mean±SD (n=3)) are expressed as $^{45}Ca$ release in the 10 minutes following addition of 20 nM thrombin/$^{45}Ca$ release in the preceding 10 minutes. The high concentration of thrombin (20 nM) was used to avoid selecting clones based on their substrate properties. Expression of library alone or F43A alone gave no thrombin signaling. Co-expression resulted in clear-cut thrombin signaling with three of the nine pools tested. The best of these was further subdivided and a clone was ultimately isolated by sib selection.

Example 4:

Epitope tagged wild type human thrombin receptor was expressed in Xenopus oocytes and agonist-induced $^{45}Ca$ release assayed as above. The peptides tested were GFIYFNPNDK (SEQ ID NO:10) and SFLLRNPNDK (SEQ ID NO:11). The peptides were extended at their carboxyl termini with native receptor sequence to circumvent solubility problems with the pentapeptides. However, the added sequence does not contribute to agonist activity. Scarborough et al., J. Biol. Chem. 267: 13146–13149 (1992); Vassallo et al., J. Biol. Chem. 267: 6081–6085 (1992). Peptides were synthesized and HPLC purified as previously described. Scarsborough et al., J. Biol. Chem. 267: 13146–13149 (1992). The data shown in FIG. 5 represent the means of duplicate determinations, and standard deviations were typically less than 20% of the means. This experiment was replicated thrice with similar results. Signaling in response to GFIYF (SEQ ID NO:3) was receptor-dependent. GFIYF (SEQ ID NO:3) did not cause signaling in uninjected oocytes or in oocytes expressing the formyl peptide receptor.

Dose response curves between wild type and GFIYF (SEQ ID NO:3) thrombin receptor to thrombin was generated in the following manner. Xenopus oocytes were microinjected with 12.5/ng cRNA encoding epitope tagged wild type thrombin receptor or a mutant thrombin receptor in which GFIYF (SEQ ID NO:3) replaced SFLLR (SEQ ID NO:4), the endogenous tethered ligand domain. Surface expression levels were shown to be similar for the two receptors by antibody binding as described. Ishii et al., J. Biol. Chem. 268: 9780–9786 (1993); Gerszten et al., Nature 368: 648–651 (1994). Thrombin-induced $^{45}Ca$ release was determined. Data shown are the means of duplicate determinations. Standard deviations were typically less than 20% of the means. This experiment was replicated thrice with similar results. As for thrombin signaling, signaling of oocytes expressing the wild type or GFIYF (SEQ ID NO:3) mutant receptors to the exogenous SFLLRN (SEQ ID NO:14) agonist peptide was also indistinguishable.

Example 5:

Formyl peptide receptor response to its classical agonist fMLF (SEQ ID NO:12) and to the new agonist derived from tethered ligand library. Human fMLF receptor cDNA was subcloned into pFROG. Xenopus oocytes were microinjected with 5 ng cRNA transcribed from this construct, cultured for 24 hours, and $^{45}Ca$ release in response to the indicated concentration of peptides was measured as described above.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for the identification of a peptide agonist for a membrane bound target receptor, which comprises:
   a. co-expressing on the surface of a living cell:
      i. said target receptor; and
      ii. a library pool of chimeric peptide presenting molecules, wherein each of said peptide-presenting molecules has membrane and external domains comprising, in the order stated:
         (1) a terminal domain cleavable by a specific peptidase;
         (2) a ligand domain having a randomized peptide sequence, said randomized peptide sequences of all said chimeric peptide presenting molecules in said pool providing a peptide library;
         (3) a linker domain, wherein said ligand domain and said linker domain together comprise a mature thrombin receptor amino terminal exodomain, with the proviso that a sequence SFLLR (SEQ ID No:4) of said exodomain is replaced by said randomized sequence; and
         (4) a CD8 transmembrane domain;
   b. adding said specific peptidase to cleave said terminal domain from said ligand domain;
   c. detecting a signal produced by said target receptor as a result of interaction of said ligand domain with said target receptor, and;
   d. repeating steps a–c, serially subdividing said pools, until a clone is ultimately isolated by sib selection, said clone encoding the chimeric peptide presenting molecule that contains the peptide agonist sequence that confers said signal, thereby identifying said peptide agonist.

2. The method of claim 1, wherein the target receptor is a G protein coupled receptor.

3. The method of claim 1, wherein the chimeric peptide presenting molecule further comprises a cytoplasmic domain that interacts with the cytoplasmic domain of the target receptor to produce the signal upon binding of the chimeric peptide presenting molecule to the receptor.

4. The method of claim 3, wherein the cytoplasmic domain of both the peptide-presenting molecule and the receptor comprise monomeric members of a dimeric signal-generating complex.

5. The method of claim 3, wherein the cytoplasmic domain of both the receptor and the chimeric peptide presenting molecule have tyrosine kinase activity.

6. The method of claim 1, wherein the peptidase is thrombin and the terminal domain of the peptide presenting molecule, together with the peptide linker and the ligand domain, comprise the thrombin receptor amino-terminal exodomain portion of the peptide presenting molecule.

7. The method of claim 1, wherein the cell is a Xenopus oocyte.

8. The method of claim 1, wherein the ligand domain is from 3 to 20 amino acids in length.

9. The method of claim 1, wherein the ligand domain is from 3 to 10 amino acids in length.

10. The method of claim 1, wherein the ligand domain is from 3 to 6 amino acids in length.

11. A peptide agonist detection system, comprising a living cell co-expressing on its surface:
   a. a membrane bound target receptor; and
   b. a library pool of chimeric peptide presenting molecules, wherein each peptide presenting molecule has membrane and external domains comprising, in the order stated:
      i. a terminal domain cleavable by a specific peptidase;
      ii. a ligand domain having a randomized peptide sequence, said randomized peptide sequences of all said chimeric peptide presenting molecules in said pool providing a peptide library;
      iii. a linker domain, wherein said ligand domain and said linker domain together comprise a mature thrombin receptor amino terminal exodomain, with the proviso that a sequence SFLLR (SEQ ID No:4) of the exodomain is replaced by said randomized sequence; and,
      iv. a CD8 transmembrane domain.

12. The agonist detection system of claim 11, wherein the cell is a Xenopus oocyte.

13. The agonist detection system of claim 11, wherein the chimeric peptide presenting molecule comprises an epitope-tagged thrombin receptor's amino terminal exodomain up to and including receptor residue aspartic acid$^{91}$ fused to the transmembrane domain of CD8 at CD8 residue isoleucine$^{162}$.

14. The method of claim 1, wherein the signal is derived from calcium ion (Ca$^{2+}$).

15. The method of claim 1, wherein the chimeric peptide presenting molecule comprises an epitope-tagged thrombin receptor's amino terminal exodomain up to and including receptor residue aspartic acid$^{91}$ fused to the transmembrane domain of CD8 at CD8 residue isoleucine$^{162}$.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO:1:

Met Met Trp Leu Leu
1               5

(2) INFORMATION FOR SEQ ID NO: 2:

(i) SEQUENCE CHARACTERISTICS:
      (A) LENGTH: 5 amino acids
      (B) TYPE: amino acid
      (C) STRANDEDNESS: single

```
           (D) TOPOLOGY: linear (ix) FEATURE:
           (A) NAME/KEY: Modified-site
           (B) LOCATION: 1
           (D) OTHER INFORMATION: /note= "Should be Formyl-Met"

(xi) SEQUENCE DESCRIPTION: SEQ ID NO:2:

Xaa Met Trp Leu Leu
1               5

(2) INFORMATION FOR SEQ ID NO:3:

(i) SEQUENCE CHARACTERISTICS:
           (A) LENGTH: 5 amino acids
           (B) TYPE: amino acid
           (C) STRANDEDNESS: single
           (D) TOPOLOGY: linear (xi) SEQUENCE DESCRIPTION: SEQ ID NO: 3:

Gly Phe Ile Tyr Phe
1               5

(2) INFORMATION FOR SEQ ID NO: 4:

(i) SEQUENCE CHARACTERISTICS:
           (A) LENGTH: 5 amino acids
           (B) TYPE: amino acid
           (C) STRANDEDNESS: single
           (D) TOPOLOGY: linear (xi) SEQUENCE DESCRIPTION: SEQ ID NO:4:

Ser Phe Leu Leu Arg
1               5

(2) INFORMATION FOR SEQ ID NO:5:

(i) SEQUENCE CHARACTERISTICS:
           (A) LENGTH: 5 amino acids
           (B) TYPE: amino acid
           (C) STRANDEDNESS: single
           (D) TOPOLOGY: linear (xi) SEQUENCE DESCRIPTION: SEQ ID NO:5:

Ser Phe Phe Leu Arg
1               5

(2) INFORMATION FOR SEQ ID NO:6:

(i) SEQUENCE CHARACTERISTICS:
           (A) LENGTH: 5 amino acids
           (B) TYPE: amino acid
           (C) STRANDEDNESS: single
           (D) TOPOLOGY: linear (xi) SEQUENCE DESCRIPTION: SEQ ID NO:6:

Thr Phe Arg Ile Phe
1               5

(2) INFORMATION FOR SEQ ID NO:7:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:7:
```

```
GTACCCCGGN NKNNKNNKNN KNNKAACCCC AATGATAAAT ATGAACCATT          50
```

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
GAATCTAGGG GCC                                                 13
```

(2) INFORMATION FOR SEQ ID NO:9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GTTCATATTT ATC                                                 13
```

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:10:

```
Gly Phe Ile Tyr Phe Asn Pro Asn Asp Lys
1               5                   10
```

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:11:

```
Ser Phe Leu Leu Arg Asn Pro Asn Asp Lys
1               5                   10
```

(2) INFORMATION FOR SEQ ID NO:12:

(i) SEQUENCE CHARACTERISTICS:
        (A) LENGTH: 3 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Should be formyl-Met"

(xi) SEQUENCE DESCRIPTION: SEQ ID NO:12:

```
Xaa Leu Phe
1
```

-continued (2) INFORMATION FOR SEQ ID NO:13:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:13:

Met Leu Phe
1

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear, (xi) SEQUENCE DESCRIPTION: SEQ ID NO:14:

Ser Phe Leu Leu Arg Asn
1          5